United States Patent [19]

Chubachi

[11] Patent Number: 5,518,608

[45] Date of Patent: May 21, 1996

[54] WATER PURITY DETERMINING DEVICE AND SYSTEM FOR PRODUCING ULTRAPURE WATER USING SUCH DEVICES

[76] Inventor: Hiroshi Chubachi, 2436, Kunugi, Fujishiro-machi, Kitasouma-gun, Ibaragi-ken, Japan

[21] Appl. No.: 183,408

[22] Filed: Jan. 18, 1994

[51] Int. Cl.⁶ .................................................. C02F 1/42
[52] U.S. Cl. .................... 210/96.1; 210/109; 210/143; 210/263
[58] Field of Search ........................... 210/96.1, 143, 210/263, 109

[56] References Cited

U.S. PATENT DOCUMENTS

| | | | |
|---|---|---|---|
| 4,563,272 | 1/1986 | Yoshida et al. | 210/96.1 |
| 4,622,133 | 11/1986 | Furuno | 210/96.2 |
| 4,698,153 | 10/1987 | Matsuzaki et al. | 210/192 |
| 4,863,608 | 9/1989 | Kawai et al. | 210/638 |

Primary Examiner—Neil McCarthy
Attorney, Agent, or Firm—Jones, Tullar & Cooper

[57] ABSTRACT

A TOC monitor for determining the quality of ultrapure water is described. The TOC monitor includes a ultraviolet oxidizer in the form of spiral tubing, having an inlet connected to a first resistivity meter and an outlet to a second resistivity meter. The difference between the measured resistivity values provides an indication of the total amount of organic carbons present in the water. Each resistivity meter includes an outer tubular electrode and an inner cylindrical electrode extending therethrough. A narrow annular space is formed therebetween for increased flow of the water, permitting an accurate measurement even at very low flow rates. Such TOC monitors are used in a ultrapure water production plant to continuously monitor the quality of water. The plant can produce ultrapure water in a continuous process and accordingly dispense with costly and contaminants producing reservoirs.

2 Claims, 5 Drawing Sheets

5,518,608

WATER PURITY DETERMINING DEVICE AND SYSTEM FOR PRODUCING ULTRAPURE WATER USING SUCH DEVICES

BACKGROUND OF INVENTION

This present invention relates to water purification and, more particularly, to an improved device for determining water purity based on its TOC (or total organic carbon) value. The present invention also relates to an ultrapure water production system incorporating such TOC monitors that produces ultrapure water in a continuous and cost effective process.

High purity water is required for many purposes, including use in semiconductor device fabrication, medicine, biology, etc. Conventionally, there are a number of techniques for purifying water, such as ultrafiltration, reverse osmosis, distillation, sorption, ion exchange, deareation, ultraviolet oxidation. They are usually employed in combinations to provide the highest purity. Water contains various impurities such as particles, ions, microorganisms, organic carbons, dissolved oxygen. For example, if water for use in fabricating semiconductor devices is not purified enough to contain trace quantities of residual organics, they tend to leave the impurities on a wafer surface leading to a significant reduction in the production yield.

Various types of devices are available for monitoring the purity of an effluent water. One measurement commonly employed is specific resistivity in megohm-cm at 25° C., a measure of ionic contamination. Pure water has a theoretical resistivity of 18.2 megohm-cm. The amount of particles present in water has also been used as a measure of water purity. Recently, a variety of so-called "TOC" monitors have been developed which measure the total amount of organic carbons present in water as a measure of water purity. The TOC monitors have enabled continuous monitoring of the quality of ultrapure water for use in a semiconductor device fabrication process. Since the organic carbons are generally electrically non-conductive, one type of TOC monitor utilizes ultraviolet or thermal oxidation to transform such organics into carbon dioxide for subsequent infrared analysis. However, this type of TOC monitor is relatively costly. Another type of TOC monitor which is simple in construction and relatively inexpensive measures the resistivity of water after oxidizing organic carbons into ionic organic acids by ultraviolet oxidation.

The TOC monitor of the latter type includes a pair of opposed electrodes for measuring the resistivity of the water flowing therebetween. Referring to FIG. 1 showing its principles of operation, the meter includes a pair of electrodes 10, 12 placed in water 14 in a beaker 16. This arrangement enables accurate resistivity measurement so long as water purity is at low levels. However, it is known in the art that as water purity approaches the theoretical level of 18.2 megohm-cm, the ultrapure water becomes adsorptive so that it takes up carbon dioxide present in the air, causing a significant drop in the water purity.

The adsorption of carbon dioxide can be minimized by placing the electrodes like electrodes 18 within closed conduits 20, 22, as shown in FIGS. 2 and 3. In the FIG. 3 arrangement, the electrodes 18 comprise two concentric tubes extending into the bent flow path. These arrangements, however, have the inherent shortcomings that, for water of high purity, measurement errors are significantly greater during very low flow rates as shown in the graph of FIG. 4.

With the arrangements, accurate resistivity measurement is very difficult for ultrapure water having a resistivity above 5 megohm-cm and flowing at lower than 100 cc/min. This is because the ultrapure water passing between the electrodes would be at very small amounts during very low flow rate conditions. Further, bubbles are generated and released from the electrodes due to electrolysis, tending to affect the measurement accuracy and reliability. It would be desirable to provide an improved arrangement which effectively increases the amount of ultrapure water flowing between the electrodes and which efficiently removes the electrolysis caused bubbles to thereby permit an accurate resistivity measurement for ultrapure water flowing at very low rates.

It is therefore the principal object of the present invention to provide an improved device for determining water purity with a view to overcoming the above-noted disadvantages of the prior art.

It is another object of the present invention to provide an improved device which measures the TOC value of an effluent water as an indication of water purity and which permits an accurate and reliable measurement of water purity even at very low flow rates.

It is a further object of the present invention to provide an improved water purity determining device which minimizes the influence of electrolysis caused bubbles on measurements.

It is still further object of the present invention to provide an improved TOC monitor arrangement in which an electrically conductive, tubular section of the conduit serves as one electrode within which the other, cylindrical electrode extends concentrically forming a narrow, annular space for increased flow of ultrapure water to be measured.

It is still another object of the present invention to provide an improved TOC monitor arrangement in which the inner cylindrical electrode is axially movable within the outer tubular electrode to vary the cell factor of the electrodes for optimum measurement.

It is a further object of the present invention to provide a ultrapure water production system incorporating improved TOC monitors that produces ultrapure water in a continuous and cost effective process.

It is still further object of the present invention to provide a ultrapure water production system in which the TOC monitors are used to permit an early detection of the deterioration of ion exchange resins for purifying the water.

SUMMARY OF THE INVENTION

These objects and other objects of the present invention are accomplished by providing a resistivity meter for measuring the resistivity of water especially during very low flow rates, comprising: a conduit having an inlet and an outlet for water; a first tubular electrode provided between the inlet and outlet of the conduit to form a part thereof; a second cylindrical electrode extending through the first tubular electrode to form an annular space therebetween for increased flow of the water during the very low flow rates; and means electrically connected to the first and second electrodes for providing a signal representative of the resistivity of the water.

In accordance with a preferred embodiment of the present invention, the second cylindrical electrode is movable relative to the first tubular electrode to vary the cell factor of the electrodes for optimum resistivity measurement.

In accordance with a further embodiment of the present invention, there is provided a TOC monitor for measuring the total amount of organic carbons present in water as an indication of the purity thereof; an ultraviolet oxidizer having an inlet and an outlet for the water and operable to oxidize organic carbons in the water into ionic organic acids; and a first resistivity meter for measuring the resistivity of the water as a measure of the ionic organic acids, the first resistivity meter comprising: a conduit having an inlet and an outlet for the water, the inlet of the conduit being coupled to the outlet of the ultraviolet oxidizer; a first tubular electrode provided between the inlet and outlet of the conduit to form a part thereof; a second cylindrical electrode extending through the first tubular electrode to form an annular space therebetween for increased flow of the water; and means electrically connected to the first and second electrodes for providing a signal representative of the resistivity of the water.

In a further embodiment of the present invention, the TOC monitor further comprises a second resistivity meter of identical construction to the first resistivity meter, the outlet of the conduit of the second resistivity meter being coupled to the inlet of the ultraviolet oxidizer; and means responsive to the outputs of the first and second resistivity meters for providing a signal indicating the difference between the measured resistivity values of the water before and after ultraviolet oxidation.

In still further embodiment of the present invention, there is provide a plant for producing and using ultrapure water, comprising: a source of untreated water; a first sampling means, including a first TOC monitor, for continuously sampling the water from the source of untreated water to measure the TOC value thereof; a water purifier for producing ultrapure water; first means provided between the source of untreated water and the water purifier and responsive to the first TOC monitor for selectively feeding the water to the water purifier or draining the water as of poor quality; a second sampling means, including a second TOC monitor, for continuously sampling the water from the water purifier to measure the TOC value thereof; a process wherein the ultrapure water is used; and second means provided between the water purifier and the process and responsive to the second TOC monitor for selectively feeding the water to the process or draining the water as of poor quality.

DETAILED DESCRIPTION OF PREFERRED EMBODIMENTS

Figure 1:
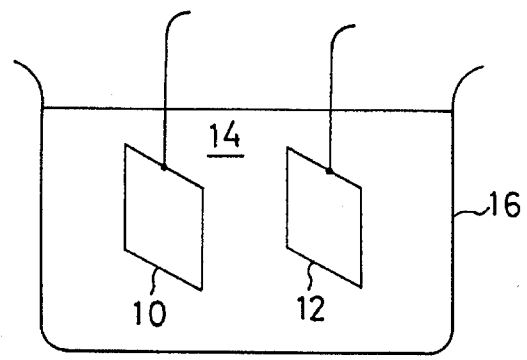
FIG. 1 is a schematic view of a typical arrangement for measuring the resistivity of water.
Figure 2:
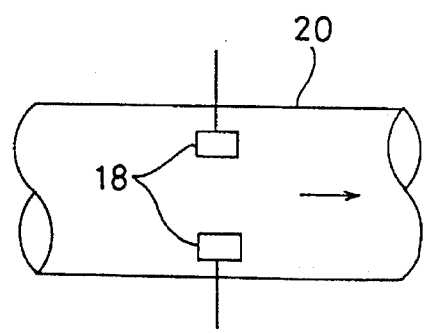
FIG. 2 is a schematic view of another arrangement including a pair of opposed electrodes placed within a conduit.
Figure 3:
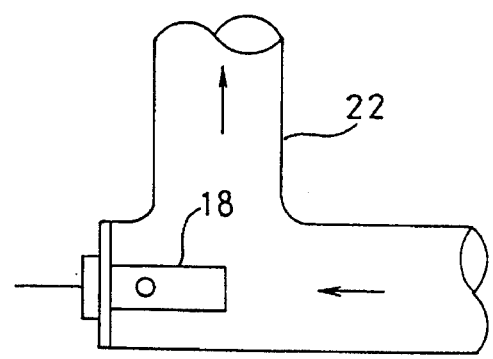
FIG. 3 is a schematic view of a further arrangement wherein a bent conduit has two concentric tubular electrodes extending therein.
Figure 4:
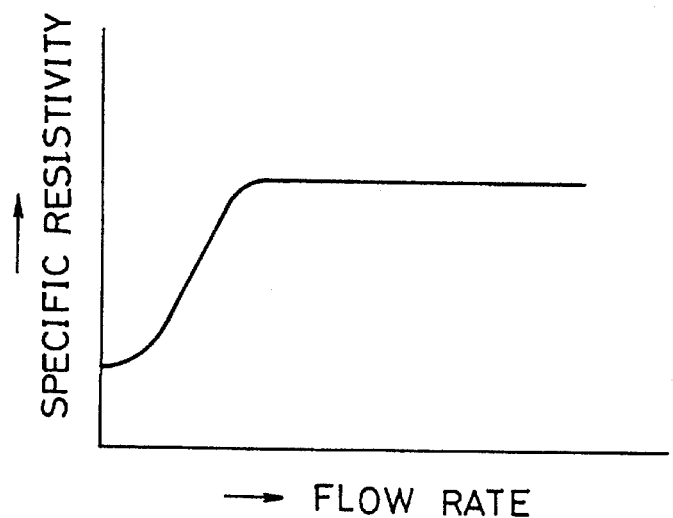
FIG. 4 is a plot of the resistivity of water as measured against flow rates, showing measurement errors generated during very low flow rates.
Figure 5:
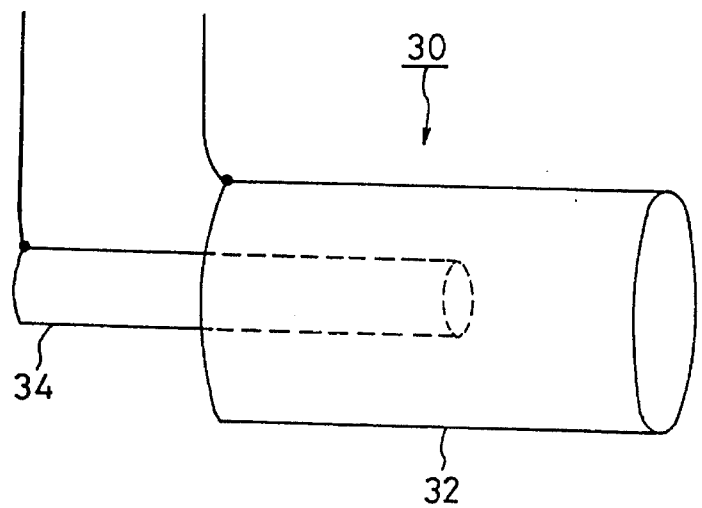
FIG. 5 is a schematic view of the general arrangement for measuring the resistivity of water, employed by the TOC monitor of the present invention.

Referring to FIG. 5, a resistivity meter 30 employed in the TOC monitor of this invention is shown diagrammatically. The resistivity meter 30 comprises an outer tubular electrode 32 and an inner cylindrical electrode 34 arranged in concentrical relationship. As is well know in the art, the resistivity meter measures the resistivity of water as a measure of ionic contamination. Although described in more detail below, it is to be noted that the TOC monitor according to this invention utilizes ultraviolet oxidation to transform organic carbons into ionic organic acids, and measures the amount of the organic acids using the resistivity meter. It should also be noted that the concentric arrangement as shown is very effective in making accurate measurement during very low flow rates, because all of the water passes between the electrodes.

Figure 6:
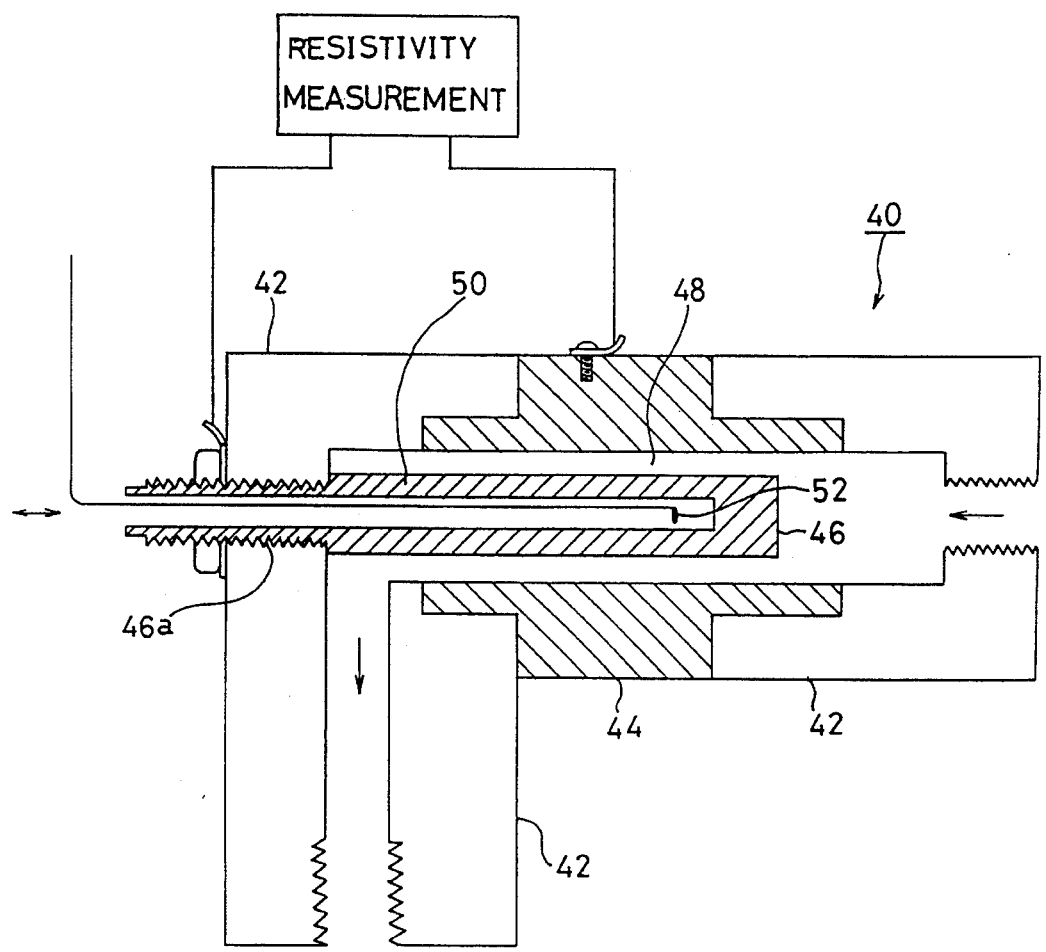
FIG. 6 is a detailed, cross-sectional view of the arrangement of FIG. 5.

FIG. 6 is a detailed view showing the construction of the resistivity meter of FIG. 5. As shown, the resistivity meter 40 includes a conduit or housing 42, an electrically conductive, tubular electrode 44 forming a part of the conduit, and an inner cylindrical electrode 46 extending through the tubular electrode 44 to form a narrow annular space 48 therebetween. The conduit or housing 42 is formed of an electrically insulating material such as DuPont's "Teflon" and the electrodes 44, 46 are formed of titanium alloys or stainless steel 316. The inner electrode 46 has formed therein an axial hole 50 for accommodating a temperature sensor 52. The temperature sensor is used to sense the acutual water temperature for subsequent translation of the resistivity at that temperature into one at 25° C.

Since the inner electrode 46 has a threaded end 46a movably engaging a threaded opening in the housing 42, it is possible to make fine adjustment of the axial position of the inner electrode to obtain the optimum cell factor of the electrodes. Experiment has shown that a cell factor of 0.05 to 0.10 is preferable for the illustrated electrode arrangement. Increasing the cell factor above the upper limit by decreasing the electrode area in fact improves the measuring performance of the TOC monitor at low flow rates. However, on the other hand, this increases the electrode resistance proportionately, placing certain constraints on the design of the electric circuitry associated with the meter as well as rendering the effects of extraneous noises significant. Accordingly, it is important to strike the balance between the cell factor and the electrode resistance so as to obtain the optimum results. Adjustment of the cell factor during measurement is possible to facilitate calibration of the TOC monitor. Preferably, both electrodes are pretreated electrochemically to minimize the generation of bubbles due to electrolysis.

Figure 7:
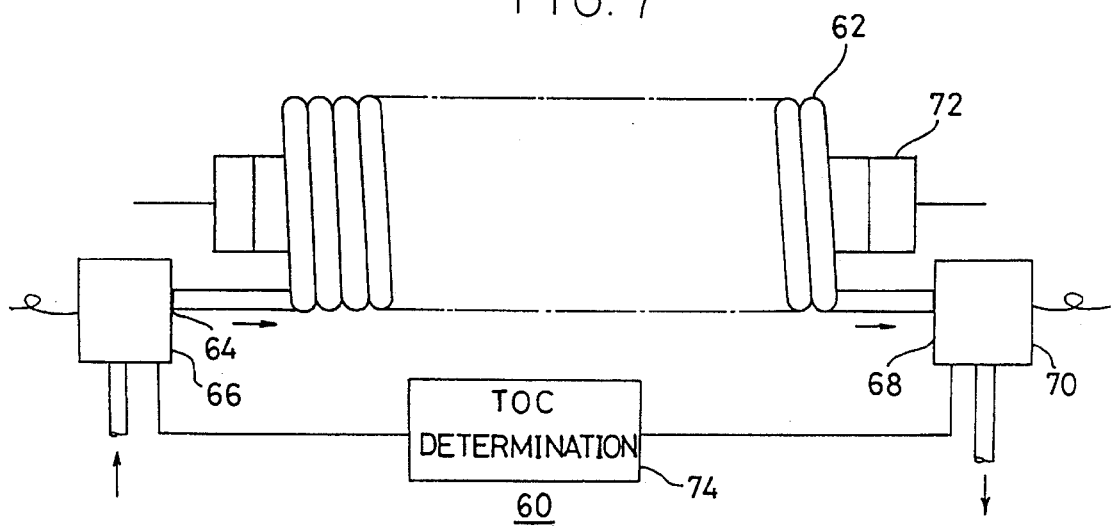
FIG. 7 is a schematic view of the overall arrangement of the TOC monitor according to the present invention in which two resistivity meters are used in combination with an ultraviolet oxidizer element.

FIG. 7 shows the overall arrangement of the TOC monitor 60 according to the present invention. It includes a spiral tubing 62 made of quartz glass and having one end connected to the outlet 64 of a first resistivity meter 66 and the other end to the inlet 68 of a second resistivity 70. The spiral tubing 62 has a ultraviolet lamp 72 extending therethrough and, preferably, it is closely wound to maximize the efficiency of ultraviolet oxidation of organic carbons in the water into ionic organic acids by the ultraviolet lamp 72. In order to minimize the residence of bubbles in the spiral tubing 62, the inner diameter of the tubing is selected to be 1.5 to 2.0 mm. Also, the diameter of the spiral is made as small as possible. The first resistivity meter 66 measures the resistivity of water before undergoing ultraviolet oxidation. The second resistivity meter 70 measures the resistivity of the water having undergone the ultraviolet oxidation during passage through the spiral tubing 62. Means 74 is provided which is responsive to the outputs of the first and second resistivity meters for providing a signal indicating the difference between the measured resistivity of the water before and after ultraviolet oxidation. This difference provides an indication of the TOC value and accordingly the purity of the water.

Figure 8:
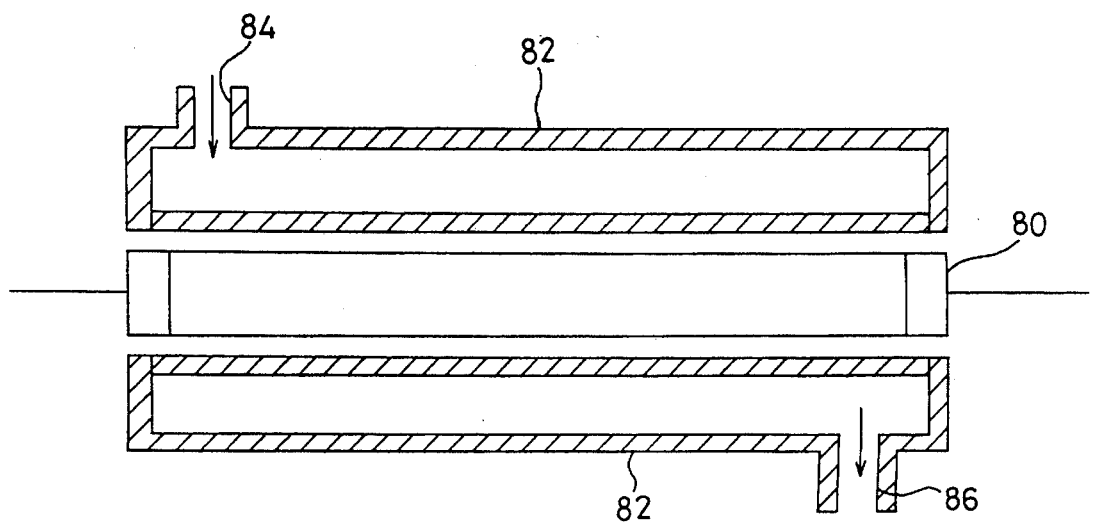
FIG. 8 is a schematic view of a typical prior art arrangement for ultraviolet oxidation of water.

This arrangement for ultraviolet oxidation is to be contrasted with a typical prior art arrangement shown in FIG. 8. In the latter arrangement, a ultraviolet lamp 80 is surrounded by an annular drum 82 having an inlet 84 and an outlet 86 located adjacent the opposite ends. It should be understood by those skilled in the art that this annular drum 82 is more likely to induce stagnation of water flow with the consequent residence of bubbles therein than does the spiral tubing 62 of this invention. With the tubing arrangement of this invention, a more uniform flow of water can be obtained to improve the accuracy of measurement.

The TOC monitor according to this invention is believed to be capable of high accuracy measurement of resistivity and accordingly the TOC value during very low flow rates. Since the ultraviolet oxidizer can be made less bulky than the prior art devices, this invention lends itself to forming a compact and integrated TOC monitor.

The TOC monitors of the present invention can be employed to monitor the quality of ultrapure water to be used in various stages in a semiconductor device fabrication plant. Water quality is checked in various processes or stages in the fabrication plant so as to selectively discharge, drain or recycle the water.

Figure 9:
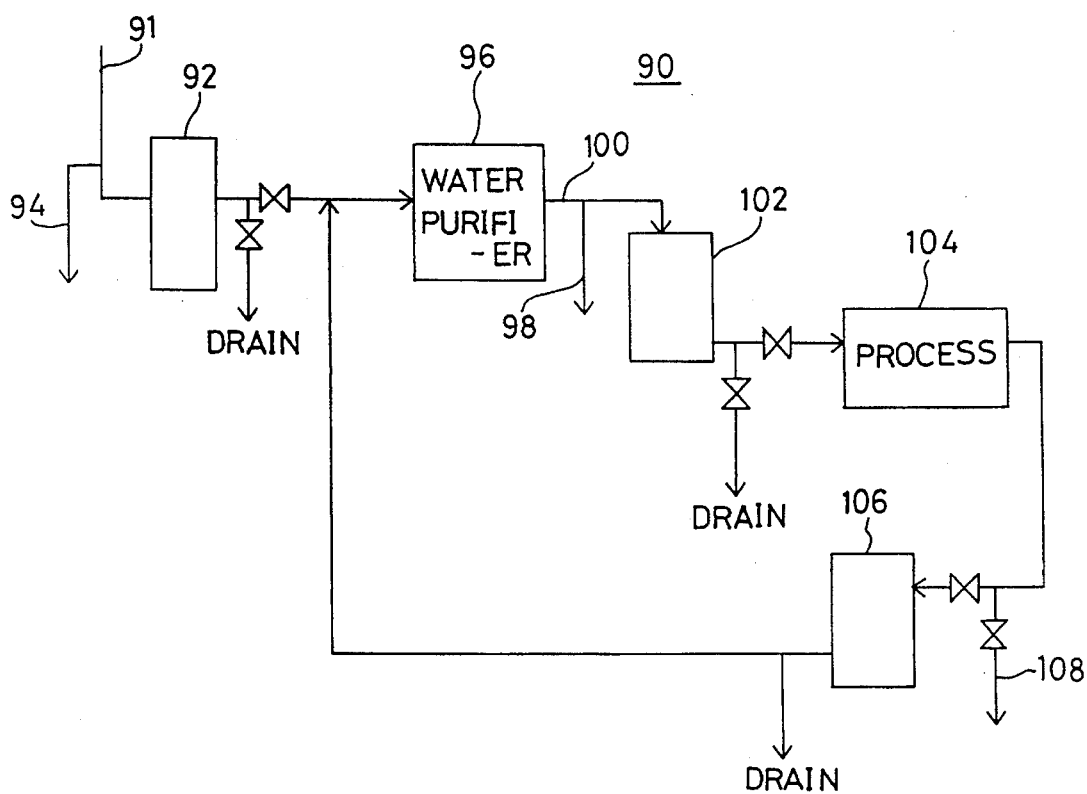
FIG. 9 is a schematic view showing a typical ultrapure water production system of the prior art.

FIG. 9 shows an example of a plant 90 wherein ultrapure water is produced in a batch process for use in fabricating semiconductor devices, for example. As shown, a supply line 91 feeds untreated or treated water to a first reservoir 92 having a a first sampling line 94 connected to the inlet thereof. The first reservoir 92 is connected to a water purifier 96 having a second sampling line 98 connected to its outlet conduit 100. The water purifier 96 purifies the water from the first reservoir 92 by utilizing ion exchange or other conventional techniques in combination to provide the desired water quality.

The output water through the purifier 96 is fed to a second reservoir 102 for temporary storage. After a certain period of time, the quality of the water flowing into the second reservoir 102 is checked by a resistivity meter provided in the second sampling line 98. If the water is determined to be of acceptable quality, the plant feeds the water to a semiconductor device fabrication process 104. The used water from the process 104 is fed to a third reservoir 106 having a third sampling line 108 connected to the inlet thereof and is selectively recycled to the inlet of the water purifier 96.

The first, second and third reservoirs are usually filled with nitrogen gas to prevent the adsorption of carbon dioxide by ultrapure water therein which would otherwise result in reducing water purity. However, this filling of nitrogen gas adds to the costs of producing ultrapure water substantially. Also, if the water in a reservor is determined not to be of acceptable quality, all of the water therein will have to be discharged at a great loss.

Also, it should be noted that in the conventional water purification plant using ion exchange, it is the resistivity of treated water which is specifically measured to monitor the deterioration of ion exchange resins employed. However, the measurement of resistivity does not provide an early enough indication of the deterioration of ion exchange resins to keep the water purifier operating at its highest efficiey. In actuality, the delay in detecting the deterioration of ion exchange resins sometimes results in a loss .of abundant water which is later decided to be discharged as of poor quality.

The use of the TOC monitors according to the present invention permits an early detection of the deterioration of ion exchange resins to thereby minimize a loss of treated water to be discarded as of poor quality.

Figure 10:
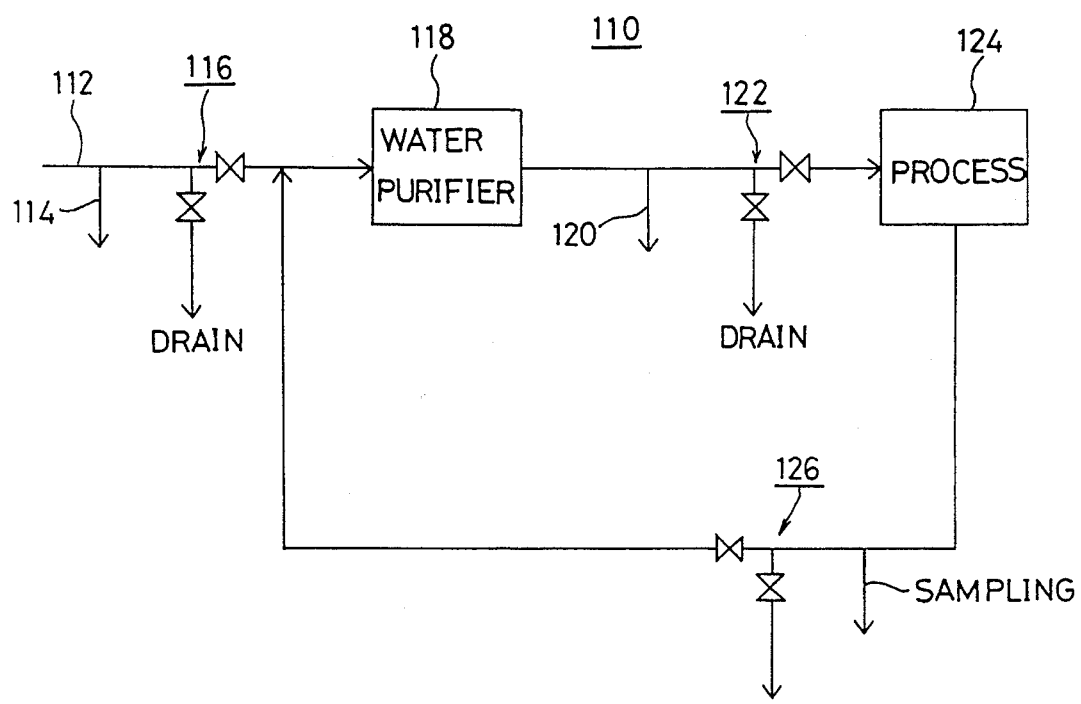
FIG. 10 is a view similar to FIG. 9 but showing an improved ultrapure water production system according to a preferred embodiment of the present invention.

FIG. 10 shows a plant 110 which produces ultrapure water in a continuous process and monitors the changing quality of the ultrapure water continuously by means of the present TOC monitors to thereby permit dispensing with costly and contaminants producing reservoirs.

As shown, the plant includes a supply line 112 having a first sampling line 114 and a valved y-connection 116 for selectively feeding water to a water purifier 118 or draining it. The first sampling line 114 has associated therewith a first TOC monitor (not shown) for continuously monitoring the quality of the water. The water purifier 118 uses ion exchange, low temperature ultraviolet oxidation and other conventional water purifying techniques in combination to purify or "polish" the water. The low temperature ultraviolet oxidation employed acts to cause water to produce hydroxyradicals directly therefrom that are effective to reduce organics. The water purifier 118 has a second sampling line 120 and a second valved y-connection 122 leading from the outlet thereof.

The output water through the purifier 118 is continuosly monitored for its TOC value by means of a second TOC monitor (not shown) associated with the second sampling line 120. This TOC monitor is coupled to a computer control system (not shown) to control the operation of the second valved y-connection 122. If the TOC value of the output water through the purifier 118 is determined to be below a predetermined level or of acceptable quality, the computer control system activates the second valved y-connection 122 to feed the water to a semiconductor device fabrication process, a pharmaceutical manufacturing process, a biological laboratory, etc, generally designated at 124. Otherwise, the water is drained or discarded as of poor quality. The used water from the process 124 is continuously monitored for its TOC value and is selectively recycled through a third valved y-connection 126 to the inlet of the water purifier 118 or drained as of poor quality.

As described above, it should be noted that this invention is based on the discovery that as the ion exchange resins deteriorate, the resulting rise in the TOC value of the output water occurs significantly earlier than the resulting drop in the resistivity of the water. In present-day ultrapure water production processes, the efficient and cost-effective operation depends greatly upon the performance of ion exchange resins. Accordingly, it would be desirable to provide a simplified and highly accurate TOC monitor that permits an early detection of the deterioration of the ion exchange resins. This invention fulfils the needs and further provides related advantages such as reduced plant and operational costs.

What is claimed is:

1. A plant for producing and using ultrapure water, comprising:

a source of untreated water;

a first sampling means, including a first TOC monitor, for continuously sampling the water from the source of untreated water to measure the TOC value thereof;

a water purifier for producing ultrapure water, said water purifier including ion exchange resins;

first means provided between the source of untreated water and the water purifier and responsive to the first TOC meter for selectively feeding the water to the water purifier or draining the water as of poor quality;

a second sampling means, including a second TOC monitor, for continuously sampling the water from the water purifier to measure the TOC value thereof and continuously monitoring the TOC value of the output water through the water purifier to permit an early detection of the deterioration of the ion exchange resins;

a process wherein the ultrapure water is used; and second means provided between the water purifier and the process and responsive to the second TOC monitor for selectively feeding the water to the process or draining the water as of poor quality.

2. A plant according to claim 1 further comprising:

a third sampling means, including a third TOC monitor, for continuously sampling the used water from the process to measure the TOC value thereof; and third means responsive to the third TOC monitor for selectively recylcing the used water to the water purifier or draining the water as of poor quality.

* * * * *